US009433521B2

(12) United States Patent
Deshmukh et al.

(10) Patent No.: US 9,433,521 B2
(45) Date of Patent: Sep. 6, 2016

(54) DISTAL TIP FOR A DELIVERY CATHETER

(71) Applicant: Medtronic, Inc., Minneapolis, MN (US)

(72) Inventors: Susheel Deshmukh, Santa Rosa, CA (US); Siyan Som, Santa Rosa, CA (US); Adam Shipley, Santa Rosa, CA (US); Matthew Spurchise, Santa Rosa, CA (US); Stephen Peter, Santa Rosa, CA (US); Shishira Nagesh, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 180 days.

(21) Appl. No.: 13/686,311

(22) Filed: Nov. 27, 2012

(65) Prior Publication Data

US 2014/0148889 A1    May 29, 2014

(51) Int. Cl.
*A61F 2/962*   (2013.01)
*A61F 2/95*    (2013.01)
*A61F 2/966*   (2013.01)

(Continued)

(52) U.S. Cl.
CPC .......... *A61F 2/962* (2013.01); *A61B 17/12022* (2013.01); *A61B 17/12145* (2013.01); *A61B 2017/00557* (2013.01); *A61B 2017/1205* (2013.01); *A61F 2/07* (2013.01); *A61F 2/95* (2013.01); *A61F 2/966* (2013.01); *A61F 2002/072* (2013.01); *A61M 25/0069* (2013.01); *A61M 25/10* (2013.01); *A61M 29/02* (2013.01);

(Continued)

(58) Field of Classification Search
CPC .......... A61F 2/958; A61F 2/95; A61F 2/966; A61F 2/954; A61F 2/07; A61F 2/91; A61F 2/90; A61F 2002/072; A61F 2002/075; A61F 2/962; A61B 17/12022; A61B 2017/1205; A61B 2017/00557; A61B 2017/12054; A61B 2017/12081; A61M 25/10; A61M 25/104; A61M 29/02; A61M 2025/0183; A61M 2025/1093; A61M 25/0069
USPC ................. 606/191–194, 200; 623/1.11–1.13
See application file for complete search history.

(56) References Cited

U.S. PATENT DOCUMENTS 3,605,725 A    9/1971  Bentov
6,551,314 B1*  4/2003  Hill et al. ........................ 606/45

(Continued)

FOREIGN PATENT DOCUMENTS

WO    WO2009137359    11/2009

OTHER PUBLICATIONS

"Interference Fit" definition accessed Aug. 20, 2015 from www.thefreedictionary.com; www.engineering-dictionary.org; and www.oxforddictionaries.com/us/.*

(Continued)

*Primary Examiner* — Melanie Tyson
*Assistant Examiner* — Rachel S Papeika

(57) ABSTRACT

Distal tips for use with delivery catheters are disclosed that are configured to maintain complete engagement between the distal tip and a distal opening of a sheath component of the delivery catheter so as to prevent separation therebetween and/or to prevent fish-mouthing of a distal leading edge of the sheath component during in vivo use. Distal tips so configured realize one or more of the objectives of safer tracking of the delivery catheter through the vasculature, safe crossing of the delivery catheter through structural components of the vasculature and heart, such as through native valves, and safe removal of the delivery catheter post deployment.

5 Claims, 8 Drawing Sheets

(51) Int. Cl.

| | | |
|---|---|---|
| *A61F 2/07* | (2013.01) | |
| *A61B 17/12* | (2006.01) | |
| *A61B 17/00* | (2006.01) | |
| *A61M 25/10* | (2013.01) | |
| *A61M 25/01* | (2006.01) | |
| *A61M 29/02* | (2006.01) | |
| *A61M 25/00* | (2006.01) | |

(52) U.S. Cl.
CPC ............... *A61M 2025/0183* (2013.01); *A61M 2025/1093* (2013.01)

(56) References Cited

U.S. PATENT DOCUMENTS

| | | | |
|---|---|---|---|
| 7,182,779 | B2 | 2/2007 | Acosta et al. |
| 7,892,273 | B2 * | 2/2011 | George et al. ............... 623/1.11 |
| 7,892,275 | B2 | 2/2011 | Hartley et al. |
| 8,182,444 | B2 | 5/2012 | Uber, III et al. |
| 8,182,522 | B2 * | 5/2012 | Sarac et al. ............... 623/1.11 |
| 2004/0193244 | A1 | 9/2004 | Hartley et al. |
| 2006/0265056 | A1 | 11/2006 | Nguyen et al. |
| 2007/0112355 | A1 | 5/2007 | Salahieh et al. |
| 2007/0112422 | A1 | 5/2007 | Dehdashtian |
| 2007/0203503 | A1 * | 8/2007 | Salahieh et al. ............... 606/108 |
| 2007/0239266 | A1 | 10/2007 | Birdsall |
| 2007/0239269 | A1 | 10/2007 | Dolan et al. |
| 2008/0071361 | A1 | 3/2008 | Tuval et al. |
| 2009/0093876 | A1 | 4/2009 | Nitzen et al. |
| 2009/0131769 | A1 * | 5/2009 | Leach et al. ............... 600/309 |
| 2009/0138015 | A1 * | 5/2009 | Conner et al. ............... 606/80 |
| 2009/0281619 | A1 | 11/2009 | Le et al. |
| 2010/0036360 | A1 * | 2/2010 | Herbowy et al. ............... 604/500 |
| 2010/0049313 | A1 | 2/2010 | Alon et al. |
| 2010/0161036 | A1 | 6/2010 | Pintor et al. |
| 2010/0286756 | A1 * | 11/2010 | Dorn et al. ............... 623/1.11 |
| 2010/0331972 | A1 | 12/2010 | Pintor et al. |
| 2011/0144735 | A1 * | 6/2011 | Hartley et al. ............... 623/1.11 |
| 2011/0251681 | A1 | 10/2011 | Shipley et al. |
| 2011/0251682 | A1 | 10/2011 | Murray, III et al. |
| 2011/0257720 | A1 * | 10/2011 | Peterson et al. ............... 623/1.11 |
| 2011/0307049 | A1 * | 12/2011 | Kao ............... 623/1.11 |
| 2011/0319989 | A1 * | 12/2011 | Lane et al. ............... 623/2.11 |
| 2012/0022628 | A1 * | 1/2012 | Dwork et al. ............... 623/1.11 |
| 2012/0184982 | A1 * | 7/2012 | Herbowy et al. ............... 606/194 |
| 2012/0239142 | A1 * | 9/2012 | Liu et al. ............... 623/2.11 |

OTHER PUBLICATIONS

U.S. Appl. No. 13/247,315, filed Sep. 28, 2011, Gallagher.

* cited by examiner

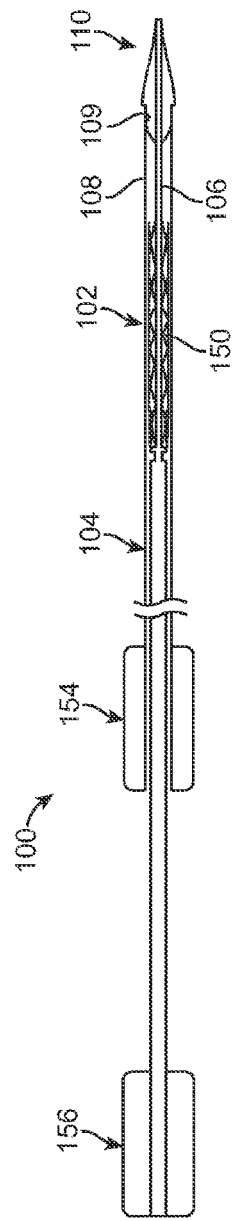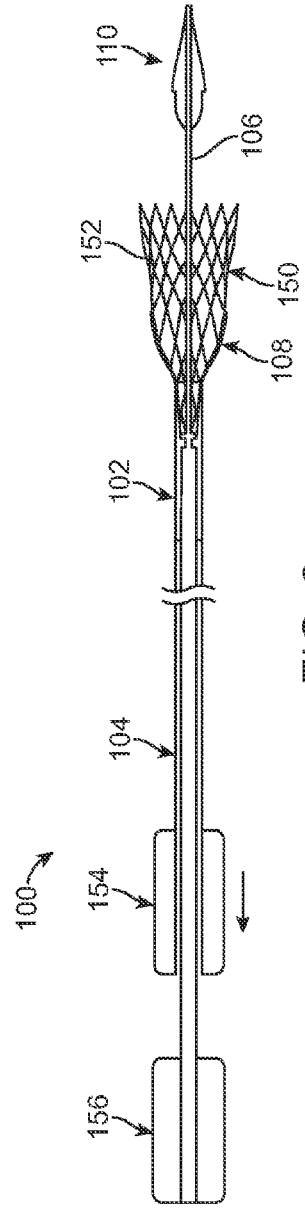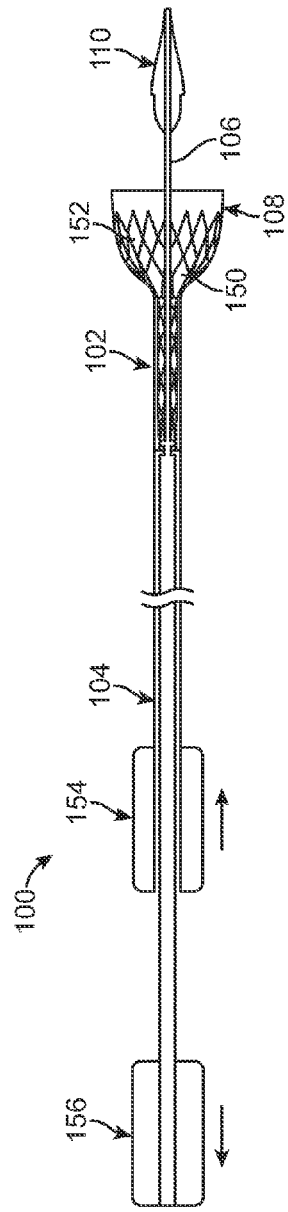

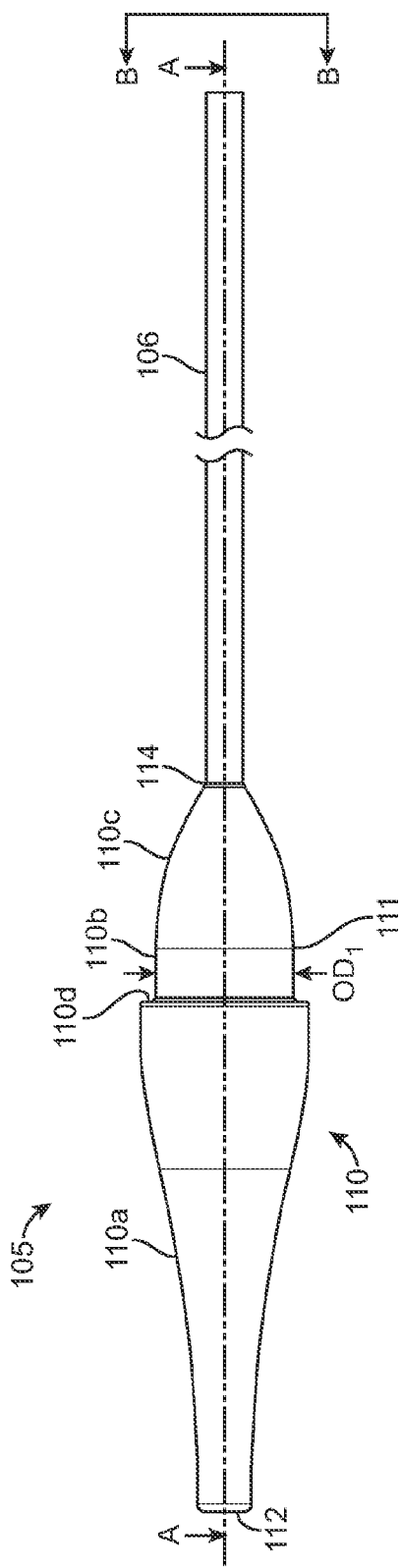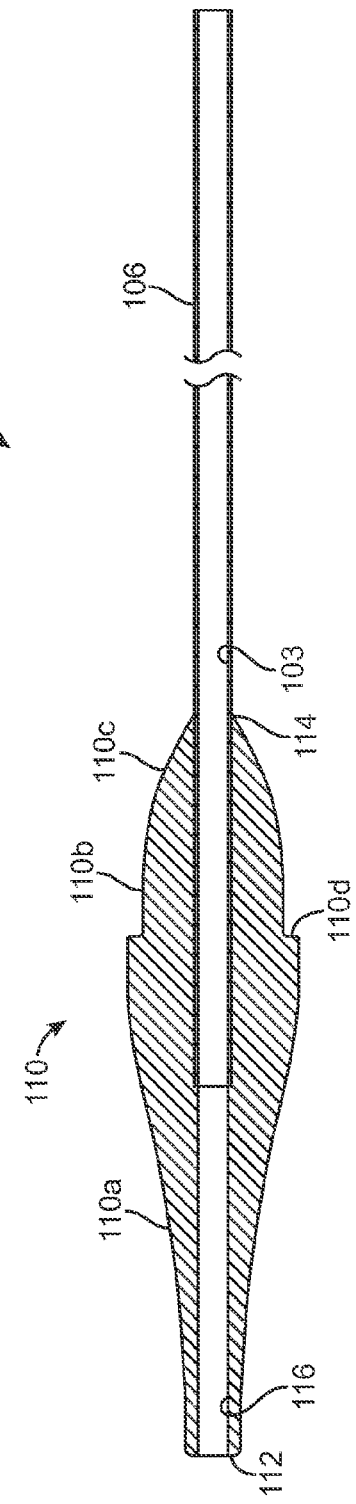
FIG. 5
FIG. 5A

DISTAL TIP FOR A DELIVERY CATHETER

FIELD OF THE INVENTION

The invention relates to a delivery catheter, such as a delivery catheter for delivering a prosthesis, and more particularly is directed to a distal tip of the delivery catheter.

BACKGROUND OF THE INVENTION

Various types and configurations of prosthetic heart valves are available or have been proposed for percutaneous transcatheter valve replacement procedures. In general, prosthetic heart valve designs attempt to replicate the functions of the native heart valve being replaced and thus will include valve leaflet-like structures mounted in some manner within an expandable stent frame, which in some instances is made of a shape memory material and construction. With such shape memory or self-expanding stent frames, the prosthetic heart valve is crimped to a desired size and held in a compressed delivery configuration within a retaining sheath, sleeve or capsule of a delivery catheter, for example, for delivery to a treatment site within the heart. In certain percutaneous transcatheter valve replacement procedures, the delivery catheter is introduced into a vessel, for example, the femoral artery or the brachial artery and tracked through the vasculature to the heart. Once the delivery catheter and more particularly the prosthetic heart valve are properly positioned with the native valve to be replaced, the retaining sheath, sleeve or capsule is retracted from the prosthetic heart valve to permit the stent frame to return to its expanded diameter for implantation within the native valve.

A delivery catheter must often navigate through tortuous anatomy as it is tracked through the vasculature to the treatment site within the heart, to include traversing the aortic arch. In the circumstance of a delivery catheter that houses a prosthetic heart valve compressed within a distal end of the retaining sheath, sleeve or capsule thereof, articulation of the catheter within the tortuous anatomy may cause a leading distal edge of the retaining sheath, sleeve or capsule to undesirably flex and/or separate from a distal tip of the delivery catheter, which is sometimes referred to as "fishmouthing." The discontinuity or disconnection that results in an incomplete closure between the distal edge of the retaining sheath, sleeve or capsule and the distal tip, as well as the "fish-mouth" shape of the leading distal edge of the retaining sheath, sleeve or capsule may make tracking of the delivery catheter more difficult and also may result in the leading distal edge of the retaining sheath, sleeve or capsule catching on and/or damaging a wall of a vessel and/or structures of the heart as the delivery catheter is tracked onward to the delivery site within the heart. Additionally, the fish-mouthed leading end of the retaining sheath, sleeve or capsule can collect and/or dislodge emboli and/or can become damaged such that a reinforcing structure of the retaining sheath, sleeve or capsule becomes exposed creating greater concern that emboli and/or dissection of a vessel may occur.

In certain delivery systems, a clinician may have the ability to partially deploy the prosthetic heart valve, evaluate a position relative to the native annulus, and then reposition the prosthetic heart valve prior to full deployment if deemed necessary. Repositioning, in turn, requires the prosthetic heart valve first be re-compressed and re-located back within the retaining sheath, sleeve or capsule. In other words, the partially deployed prosthetic heart valve must be "recaptured" by the delivery catheter, and in particular be returned to within the retaining sheath, sleeve or capsule thereof. Often once the prosthetic heart valve is recaptured, the distal edge or end of the retaining sheath, sleeve or capsule may have experienced some permanent deformation and consequently have a greater inner diameter than before the initial deployment of the prosthetic heart valve. In such a situation, a gap may occur between the distal edge of the retaining sheath, sleeve or capsule and the distal tip, which may result in the delivery catheter having poor or reduced tracking capabilities after the recapture and to suffer from other deficiencies as noted above with regard to incomplete closure between the distal tip and the sheath, sleeve or capsule.

In light of the above, a need exists for a prosthetic heart valve delivery system that addresses the problems of fishmouthing and/or other discontinuities/disconnections between a distal edge of a retaining sheath, sleeve or capsule and a distal tip of the delivery catheter that may occur during tracking and/or removal of the delivery catheter and/or during recapture of the prosthetic heart valve prior to full deployment of the prosthesis at a treatment site within the heart.

BRIEF SUMMARY OF THE INVENTION

Embodiments hereof are directed to distal tips for use with delivery catheters that are configured to maintain complete engagement between the distal tip and a distal opening of a sheath component of the delivery catheter so as to prevent separation therebetween and/or to prevent fishmouthing of a distal leading edge of the sheath component during in vivo use. Embodiments hereof are configured to realize one or more of the objectives of safer tracking of the delivery catheter through the vasculature, safe crossing of the delivery catheter through structural components of the vasculature and heart, such as through native valves, and safe removal of the delivery catheter post deployment.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a delivery catheter in a delivery configuration in accordance with an embodiment hereof.

FIG. 2 depicts the delivery catheter of FIG. 1 in a deployment configuration with a prosthetic heart valve in a partially deployed configuration.

FIG. 3 depicts the delivery catheter of FIG. 1 in a recapture configuration with the partially deployed prosthetic heart valve, as depicted in FIG. 2, being recaptured and compressed in accordance with an embodiment hereof.

FIG. 5 is an enlarged view of a distal inner portion of the delivery catheter of FIG. 1 in accordance with an embodiment hereof.

FIG. 5A is a sectional view of the delivery catheter distal inner portion shown in FIG. 5 taken along line A-A thereof.

DETAILED DESCRIPTION OF THE INVENTION

Figure 4:
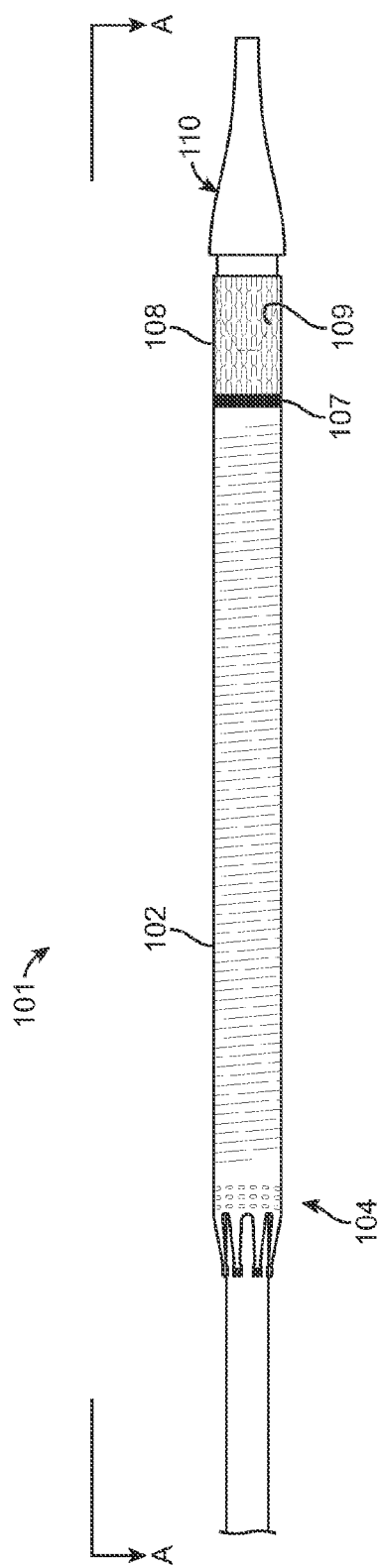
FIG. 4 is an enlarged view of a distal portion of the delivery catheter of FIG. 1 in accordance with an embodiment hereof.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of embodiments hereof are in the context of transcatheter delivery systems for delivering a prosthetic heart valve within a native heart valve, the invention may also be used where it is otherwise deemed useful with other transcatheter delivery systems for endoluminally delivering various other prostheses within the vasculature. Furthermore, there is no intention to be bound by any expressed or implied theory presented in the preceding technical field, background, brief summary or the following detailed description.

FIGS. 1-3 illustrate a delivery catheter 100 that is configured for endoluminal transcatheter repair/replacement of a defective heart valve. Delivery catheter 100 is depicted in a delivery configuration in FIG. 1 with an exemplary prosthetic heart valve 150 loaded within a distal capsule section 102 of a tubular sheath component 104. In general terms, prosthetic heart valve 150 includes a stent frame maintaining a valve structure (tissue or synthetic) within the stent frame and having a normal, expanded arrangement and being collapsible to a compressed delivery arrangement for loading within delivery catheter 100. The stent frame is constructed to self-deploy or self-expand when released from delivery catheter 100. In an embodiment, a prosthetic heart valve useful with embodiments hereof can be a prosthetic heart valve as disclosed in U.S. Pat. Appl. Pub. No. 2008/0071361 to Tuval et al., which is incorporated by reference herein in its entirety. Other non-limiting examples of transcatheter heart valve prostheses useful with systems and methods of the present disclosure are described in U.S. Pat. Appl. Pub. No. 2006/0265056 to Nguyen et al., U.S. Pat. Appl. Pub. No. 2007/0239266 to Birdsall, and U.S. Pat. Appl. Pub. No. 2007/0239269 to Dolan et al., each of which is incorporated by reference herein in its entirety.

In the delivery configuration of FIG. 1, distal capsule section 102 is disposed over prosthetic heart valve 150 to compressively retain the prosthetic heart valve in crimped engagement with a tubular inner shaft or member 106. A flareable funnel segment 108 of distal capsule section 102 is of a shape memory construction and is distally spaced from prosthetic heart valve 150 in the delivery configuration of FIG. 1. In an embodiment, funnel segment 108 may be of a length in the range of 0.5 cm to 1 cm. After either recapture and/or full deployment of prosthetic heart valve 150, the shape memory property imparted to funnel segment 108 causes the funnel segment to substantially return to a tubular reduced diameter state illustrated in FIG. 1, as more fully described below.

Delivery catheter 100 is depicted in a deployment configuration in FIG. 2 with prosthetic heart valve 150 partially deployed/expanded. Distal capsule section 102 is shown proximally retracted relative to prosthetic heart valve 150 to permit a distal region 152 of prosthetic heart valve 150 to self-expand. Funnel segment 108 does not resist or impede this expansion but instead is expanded by distal region 152 of prosthetic heart valve 150 to a shape generally corresponding with that of the deploying distal region 152. At this stage of deployment of prosthetic heart valve 150, if a clinician deems the positioning within a native heart valve to be repaired as correct, distal capsule section 102 is proximally retracted relative to prosthetic heart valve 150 to permit full release and deployment of prosthetic heart valve 150 there from.

When a partial deployment positioning of prosthetic heart valve 150 within the native heart valve is deemed less than optimal, prosthetic heart valve 150 can be resheathed or recaptured within distal capsule section 102 by distally advancing sheath component 104, as generally depicted in a recapture configuration of delivery catheter 100 shown in FIG. 3. To perform this resheathing/recapture function, funnel segment 108, in the expanded condition, readily slides along an exterior of prosthetic heart valve 150, and effectively serves as a buffer between the structure of the prosthetic heart valve 150 and a stiffer proximal portion of distal capsule section 102. As distal capsule section 102 is distally advanced over expanded distal region 152 of prosthetic heart valve 150, the prosthetic heart valve is forcibly compressed back to the initial, compressed delivery configuration depicted in FIG. 1. Due to the shape memory property of funnel segment 108, as funnel segment 108 is maneuvered distal of the collapsing prosthetic heart valve 150, funnel segment 108 substantially returns or self-transitions back to the tubular reduced diameter state depicted in FIG. 1. However, it would be understood by one of ordinary skill in the art that some deformation and/or increase in diameter is likely to have been experienced by at least a distalmost end of funnel segment 108 after resheathing/recapture of the prosthetic heart valve and/or after full deployment thereof.

In general, deployment of prosthetic heart valve 150 is accomplished by proximal movement of sheath component 104 relative to inner shaft 106 and prosthetic heart valve 150 through use of a first actuator mechanism or control 154, with a second actuator mechanism or control 156 being used to provide proximal forces to inner shaft 106 relative to sheath component 104 so as to retract partially expanded prosthetic heart valve 150 into distal capsule section 102, when recapture is desired. First and second actuator mechanisms 154, 156 are only generally depicted and may take any suitable form for performing the above-noted functions as would be apparent to one of ordinary skill in the art. For instance in an embodiment, each of first and second actuators 154, 156 may be screw-gear mechanisms that are actuated by a clinician. Sheath component 104 and inner shaft 106 are generally thin-walled, flexible tubular structures of a polymeric material, such as polyethylene block amide copolymer, polyvinyl chloride, polyethylene, polyethylene terephthalate, polyamide, or polyimide, and may be formed from one or more tubular components. In embodiments hereof, distal capsule section 102 and funnel segment 106 may be composite tubular structures of a polymeric material that is reinforced with a braided or webbed layer of a suitable biocompatible metal or metal alloy, such as nitinol, with funnel segment 106 having a nitinol reinforcement layer that permits the funnel segment to be shape set in the shape memory configuration shown in FIG. 1. In other embodiments hereof, prosthesis delivery systems and components thereof as shown and described in U.S Pat. Appl. Pub. No. 2011/0251681 to Shipley et al. or in U.S Pat. Appl. Pub. No. 2011/0251682 to Murray, III et al., each of which is incorporated by reference herein in its entirety, may be adapted for use herein.

Delivery catheter 100 includes an atraumatic distal tip 110 that is a plug style tip in accordance with an embodiment hereof. Distal tip 110 is attached at a distal end of inner shaft 106 to engage with a distal opening 109 of sheath component 104 when delivery catheter 100 is in a delivery configuration, which includes during initial tracking of delivery catheter 100 to a treatment site, after recapture of prosthetic heart valve 150 and during subsequent repositioning of delivery catheter 100, and during removal of delivery catheter 100 from the vasculature at the completion of the interventional procedure. Distal tip 110 is disengaged from distal opening 109 of sheath component 104 during partial and/or full deployment of prosthetic heart valve 150 when delivery catheter 100 is in a deployment configuration. With reference to FIG. 5A, which is an enlarged sectional view of a distal inner portion 105 of delivery catheter 100 in accordance with an embodiment hereof, a guidewire lumen 116 is defined from a proximal end 114 to a distal end 112 of distal tip 110 that is a continuation of a guidewire lumen 103 of inner shaft 106, with guidewire lumen 103 extending to a proximal end of delivery catheter 100 as would be understood by one of skill in the art. Guidewire lumens 116, 103 are sized to receive a guidewire therethrough for tracking delivery catheter 100 there over within the vasculature and structures of the heart to a treatment site. In embodiments hereof, distal tip 110 is secured to inner shaft 106 by means such as gluing, welding and over-molding, such as by injection molding.

Figure 4A:
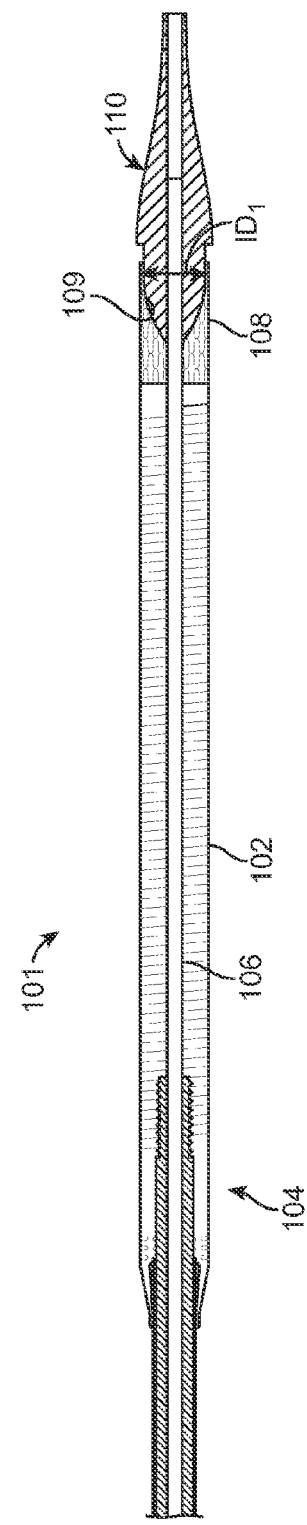
FIG. 4A is a sectional view of the delivery catheter distal portion shown in FIG. 4 taken along line A-A thereof.

With reference to FIGS. 4 and 4A, which are enlarged views of a distal portion 101 of delivery catheter 100 in accordance with an embodiment hereof, distal opening 109 is defined by funnel segment 108 of distal capsule section 102. Distal tip 110 forcibly interacts with distal opening 109 in order to be retained by distal opening 109 when delivery catheter 100 is in the delivery configuration. By retained by distal opening 109 of sheath component 104 it is meant that distal tip 110 is forcibly secured or held within distal opening 109 such that during tracking of delivery catheter 100 through the tortuous anatomy of a patient, unintentional or inadvertent longitudinal separation of distal tip 109 from sheath component 104 is prevented. In other words, a longitudinal position of distal tip 110 relative to distal opening 109 is maintained when delivery catheter 100 is in the delivery configuration. In such an arrangement, distal tip 110 continually radially supports distal opening 109 of sheath component 104 during advancement of delivery catheter 100 through the vasculature and structures of the heart to thereby also eliminate fish-mouthing of funnel segment 108 of distal capsule section 102. However, relative movement between distal tip 110 and sheath component 108 that is caused by a clinician actuating or manipulating one or both actuation mechanisms 154, 156 will result in the separation of distal tip 110 from distal opening 109 to permit deployment of prosthetic heart valve 150, as would be understood by one of ordinary skill in the art.

Figure 5B:
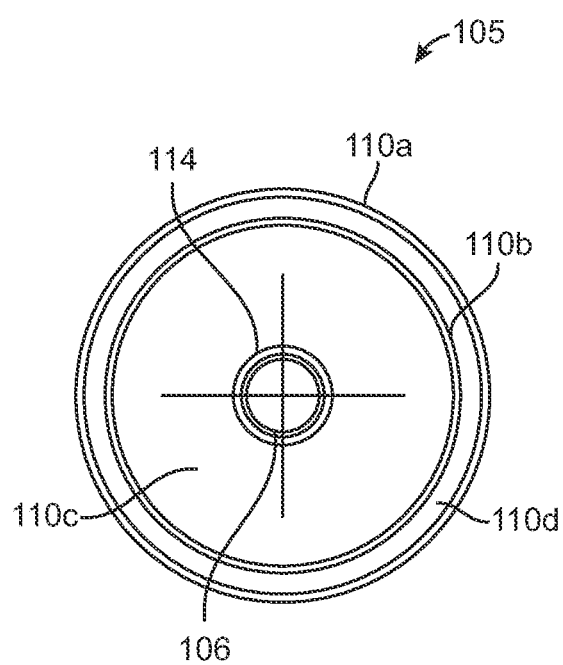
FIG. 5B is a proximal end view of the delivery catheter distal inner portion shown in FIG. 5 in a direction of line B-B thereof.

In an embodiment, an interference or tight plug-like compression fit of distal tip 110 within distal opening 109 of sheath component 104 permits distal tip 110 to be retained by distal opening 109. With reference to FIGS. 5, 5A and 5B, which are enlarged views of distal inner portion 105 of delivery catheter 100 in accordance with an embodiment hereof, distal tip 110 is a molded component of a polymeric material that defines or includes a distally tapered segment 110a, a proximally tapered segment 110c with a shelf segment 110b therebetween. In embodiments hereof, distal tip 110 may be formed from suitable biocompatible polymeric materials, such as polyamides, polyether block amides, polyurethanes, polyurethane alloys, Chrono-Prene™, and C-Flex™. Distally tapered segment 110a and shelf segment 110b are demarcated by a proximally facing abutment surface 110d that forms a radially extending circumferential ridge around distal tip 110. Distally tapered segment 110a extends between abutment surface 110d and distal end 112 of distal tip 110 and has a slightly longer taper than a conventional distal tip to provide for superior tracking along a guidewire. Shelf segment 110b is a length of distal tip 110 with substantially a constant outer diameter $OD_1$ that proximally extends from abutment surface 110d to a proximal point or end 111 of shelf segment 110b that is a point where an outer diameter of distal tip 110 begins to proximally taper or reduce from outer diameter $OD_1$. Thereafter or from proximal end 111 of shelf segment 101b to proximal end 114 of distal tip 110 is defined proximally tapered segment 110c. Proximally tapered segment 110c has a long gradual taper from shelf segment proximal end 111 to distal tip proximal end 114 making for a smoother transition with inner shaft 106.

In interference and compression fit embodiments in accordance herewith, outer diameter $OD_1$ of distal tip shelf segment 110b is greater than an inner diameter $ID_1$ of distal opening 109 of sheath component 104 in order to have an interference and/or compression fit therewith so as to be retained by distal opening 109 when delivery catheter 100 is in the delivery configuration. Advantageously the greater $OD_1$ of distal tip shelf segment 110b results in shelf segment 110b still being retained by distal end 109 of funnel segment 108 after resheathing/recapture of prosthetic heart valve 150 and/or after full deployment thereof, even if some deformation and/or increase in inner diameter $ID_1$ has occurred during these functions.

In embodiments hereof, interference between shelf segment 110b of distal tip 100 and distal opening 109 of sheath component 104 may be in the range of 1% to 20% volume interference. In another embodiment, distal tip 110 is a molded component of a compressible or deformable material, such that distal tip shelf segment 110b is retained within distal opening 109 of sheath component 104 by compression of $OD_1$ of shelf segment 110b within distal opening 109. In accordance with another embodiment, an oversized compressible distal tip 110 permits a clinician to enter delivery catheter 100 into the patient's body via a smaller French size introducer by compressing distal tip 110 to fit within such an introducer, and thereafter once distal tip 110 enters the vasculature it will expand to its original oversized diameter to provide superior tracking of delivery catheter 100 and protection from fish-mouthing. Compressible or deformable distal tips in accordance with embodiments hereof may be formed from a material such as ChronoPrene™ 15A or 75A available from AdvanSource Biomaterials Corp. of Wilmington, Mass. or a softer PEBAX, for example.

Figure 6:
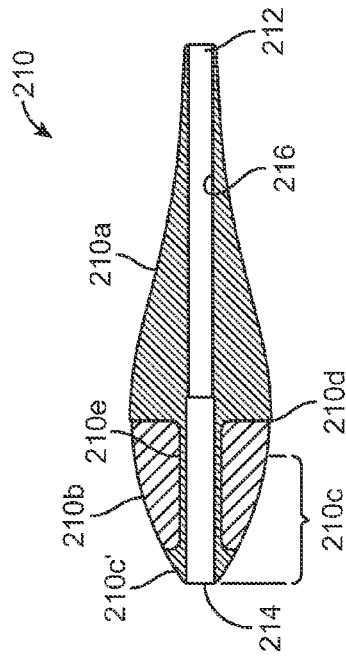
FIG. 6 is a side view of a distal tip in accordance with another embodiment hereof, with FIG. 6A being a cross-section taken along line A-A.
Figure 6A:
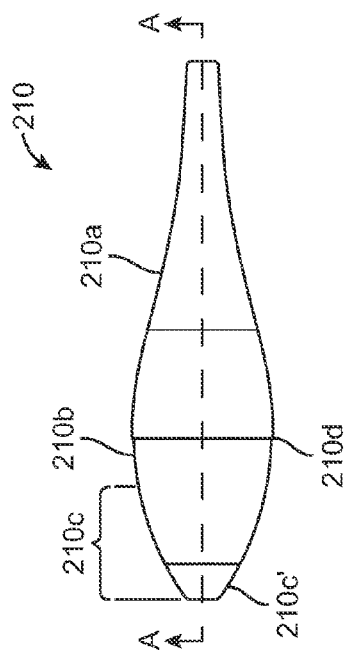
Figure 7:
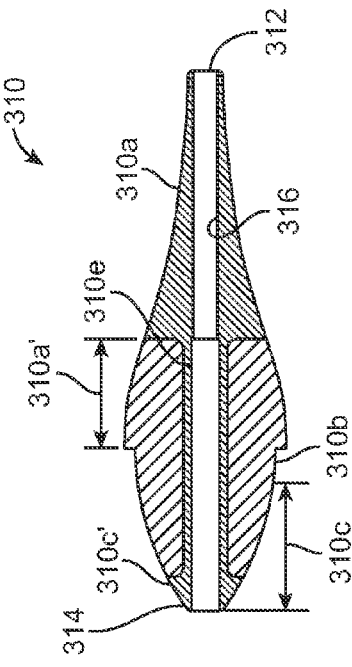
FIG. 7 is a side view of a distal tip in accordance with another embodiment hereof, with FIG. 7A being a cross-section taken along line A-A.
Figure 7A:
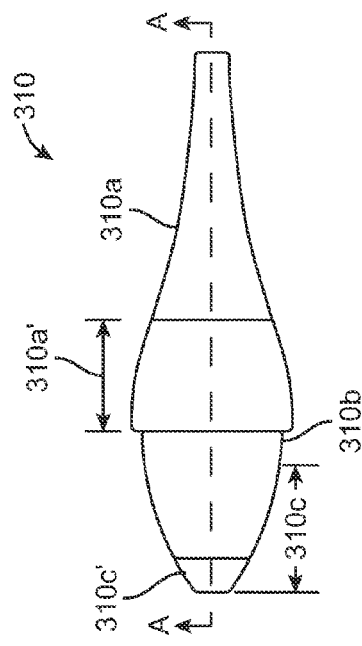

FIG. 6 is a side view of a distal tip 210 in accordance with another embodiment hereof, with FIG. 6A being a cross-section taken along line A-A and FIG. 7 is a side view of a distal tip 310 in accordance with another embodiment hereof, with FIG. 7A being a cross-section taken along line A-A. Distal tips 210, 310 are described herein as alternate components of delivery catheter 100. As well it should be understood to one of skill in the art that the embodiments of FIGS. 6 and 7 may be adapted for use with features described with reference to other embodiments hereof and only features and functions that differ from those described with reference to other embodiments will be detailed herein.

Distal tips 210, 310 are two-piece molded components having a first piece of an atraumatic first polymeric material, such as polyamide, polyether block amide, or polyurethane, and a second piece of a compressible second polymeric material, such as ChronoPrene™ 15A or 75A, a soft polyether block amide, a soft polyurethane alloy or C-Flex™, for example. The first piece of distal tips 210, 310 includes at least a distalmost portion of distally tapered segments 210*a*, 310*a* and at least a proximalmost portion 210*c'*, 310*c'* of proximally tapered segments 210*c*, 310*c* with guidewire lumen connecting portions 210*e*, 310*e* therebetween such that guidewire lumens 216, 316 are defined by the first piece from a proximal end 214, 314 to a respective distal end 212, 312 of distal tips 210, 310. A second piece of distal tips 210, 310 includes shelf segments 210*b*, 310*b* and a remaining distal portion of proximally tapered segments 210*c*, 310*c*. With reference to distal tip 210, the entire distally tapered segment 210*a* is a part of the first piece of the first material, whereas with reference to distal tip 310 a proximal portion 310*a'* of distally tapered segment 310*a* forms a portion of the second piece of the second material. In an embodiment hereof, the second piece of a respective distal tip 210, 310 may be over molded onto the first piece of the respective distal tip 210, 310 as would be recognized by one of skill in the art.

In the two material embodiments of FIGS. 6 and 7, the squeezable or compressible second material is along shelf segments 210*b*, 310*b* of distal tips 210, 310, which is the portion of the distal tips that fixates the distal tip within a distal opening of the delivery catheter, and is also along proximal portion 310*a'* of distal tip 310, which permits an overall diameter of distal tip 310 to be reduced to fit within a smaller French size introducer, as previously discussed above. In contrast, the first polymeric material is a conventional tip material that maintains strong bond strength with an inner shaft or member of the delivery catheter as well as reduces tracking forces of the distally tapered segments 210*a*, 310*a* of distal tips 210, 310 as each is tracked along a guidewire to a treatment site.

In another embodiment, the distally tapered segments 210*a*, 310*a* of distal tips 210, 310 of the first polymeric material may also be of a compressible material, such as ChronoPrene™ 15A or 75A, a soft polyether block amide, a soft polyurethane alloy or C-Flex™, for example, that has a different compressibility from a compressibility of the second material from which at least shelf segments 210*b*, 310*b* of distal tips 210, 310 are formed. In another embodiment, the distally tapered segments 210*a*, 310*a* of distal tips 210, 310 of a compressible material may have a lubricous coating, such as a coating that includes siloxane. In another two material embodiment, shelf segments 210*b*, 310*b* of distal tips 210, 310 maybe formed from a suitable polymeric material of a first durometer hardness and at least a portion of the remainder of the distal tip, such as distally tapered segments 210*a*, 310*a* of distal tips 210, 310, may be formed from a suitable polymeric material of a second durometer hardness.

In another embodiment, a first material of distally tapered segment 210*a* of distal tip 210 may have a first radiopacity and a second material of shelf segment 210*b* of distal tip 210 may have a second radiopacity in order to permit a clinician to determine or discern where abutment surface 210*d* and, by association, the distalmost point of shelf segment 210*b* are located relative to a marker band 107 that is disposed proximate to distal opening 109 of sheath component 104. By permitting better visualization of these two reference points, the clinician can more readily confirm complete closure or engagement of shelf segment 210*b* within distal opening 109 of sheath component 104 prior to tracking the delivery catheter to a treatment site and post-delivery prior to removal. Complete closure is preferable to maintain engagement between the distal tip and the sheath component distal opening so as to prevent separation and/or fish-mouthing and thereby realize one or more of the objectives of embodiments hereof, which include safer tracking of the delivery catheter through the vasculature, safe crossing of the delivery catheter through structural components of the vasculature and heart, such as through native valves, and safe removal of the delivery catheter post deployment. In addition, better visualization provided by the dual shades of radiopacity also prevents over-closure of the distal tip within the distal opening of the sheath component, which otherwise may cause damage to the delivery catheter and/or increase the overall profile of the delivery catheter and/or create an edge thereto that could inadvertently cause damage to the vasculature or structural components thereof during removal of the delivery catheter post deployment.

In an embodiment of a dual shade radiopaque distal tip 210 in accordance herewith, distally tapered segment 210*a* may be formed from a polymeric material loaded with a first percentage by weight of a radiopaque material and shelf segment 210*b* may be formed from the same polymeric material, or a different but compatible polymeric material, or a different polymeric material modified with a suitable compatibilizer loaded with a second percentage by weight of the radiopaque material. In embodiments hereof, the first percentage by weight of the radiopaque material may be preferably 5% to 25%, but may also be as large as 75%, and the second percentage by weight of the radiopaque material may be preferably 25% to 75%, but may also be as small as 5%. In one such embodiment, the polymeric material may be a polyurethane and the radiopaque material may be barium sulfate ($BaSO_4$). In another embodiment of a dual shade radiopaque distal tip 210 in accordance herewith, distally tapered segment 210*a* may be formed from a first polymeric material loaded with a first radiopaque material and shelf segment 210*b* may be formed from a second polymeric material loaded with a second radiopaque material. In one such embodiment, the first polymeric material may be a polyurethane, the second polymeric material may be Chronoprene 15A or 75A or a soft PEBAX, and the first and second radiopaque material may be selected to be different ones of barium sulfate ($BaSO_4$), bismuth trioxide, bismuth oxychloride, bismuth subcarbonate, and tungsten.

Figure 8:
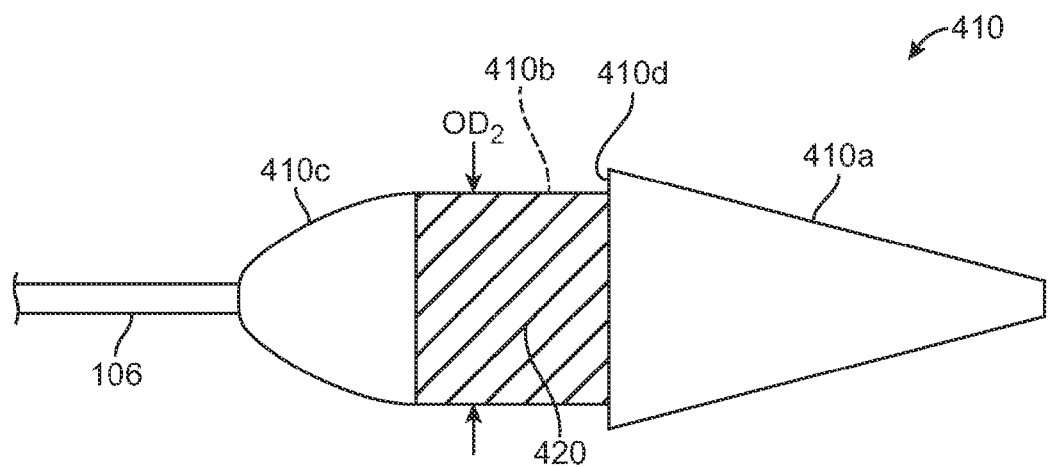
FIG. 8 is a side view of a distal tip in accordance with another embodiment hereof.
Figure 9:
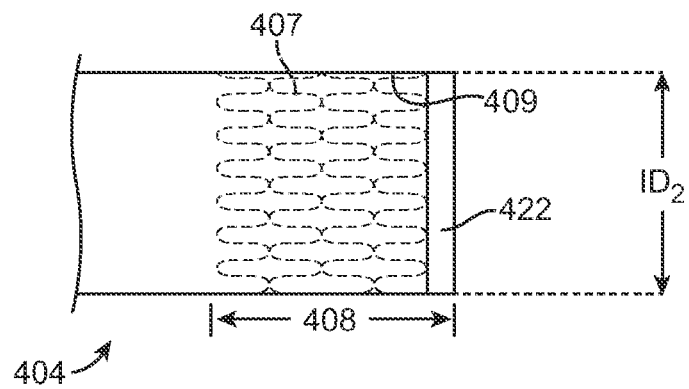
FIG. 9 is a side view of a distal end of a sheath component of a delivery catheter for use with the distal tip of FIG. 8 in accordance with an embodiment hereof.

FIG. 8 is a side view of a distal tip 410 in accordance with another embodiment hereof with FIG. 9 being a side view of distal opening 409 of sheath component 404 of delivery catheter 100, and more particularly of a modified funnel segment 408 that defines distal opening 409 for use with distal tip 410 in accordance with an embodiment hereof. Distal tip 410 and modified funnel segment 408 are described herein as alternate components of delivery catheter 100. As well it should be understood to one of skill in the art that the embodiment of FIGS. 8 and 9 may be adapted for use with features described with reference to other embodiments hereof and only features and functions that differ from those described with reference to other embodiments will be detailed herein.

Distal tip 410 is a molded component of a polymeric material that defines or includes a distally tapered segment 410a and a proximally tapered segment 410c with a shelf segment 410b therebetween. Shelf segment 410b is a length of distal tip 410 with substantially a constant outer diameter $OD_2$ that proximally extends from abutment surface 410d to a proximal point or end 411 of shelf segment 410b that is a point where an outer diameter of distal tip 410 begins to proximally taper or reduce from outer diameter $OD_2$. Distal tip shelf segment 410b engages with distal opening 409 of tubular sheath 104 when delivery catheter 100 is in a delivery configuration and disengages from distal opening 409 when delivery catheter 100 is in a deployment configuration. In the embodiments of FIGS. 8 and 9, outer diameter $OD_2$ of distal tip shelf segment 410b is equal to or slightly less than an inner diameter $ID_2$ of distal opening 409 of sheath component 104 in order to be slidably received therein.

Distal tip 410 is retained within distal opening 409 due to magnetic attraction therebetween, with the magnetic attraction being strong enough to assure that distal tip 410 remains seated within distal opening 409 to maintain engagement between distal tip 410 and sheath component distal opening 409 and thereby prevent separation and/or fish-mouthing. Accordingly the configuration of the embodiment of FIGS. 8 and 9 realizes one or more of the objectives of embodiments hereof, which includes safer tracking of the delivery catheter through the vasculature, safe crossing of the delivery catheter through structural components of the vasculature and heart, such as through native valves, and safe removal of the delivery catheter post deployment. Distal tip 410 defines a guidewire lumen therethrough that is a continuation of guidewire lumen 103 of inner shaft 106 and is attached to inner shaft 106 in any suitable manner as previously described above.

In an embodiment, magnetic attraction between distal tip 410 and distal opening 409 of sheath component 404 is accomplished by a magnetized element 420 disposed on or within distal tip shelf segment 410b that magnetically attracts a magnetic element 422 disposed at distal opening 409 of funnel segment 408. In FIG. 9, a shape memory nitinol layer 407 is shown disposed proximal of magnetic element 422 within funnel segment 408 and is the feature of funnel segment 408 that causes the funnel segment to substantially return to the tubular reduced diameter state illustrated in FIG. 9 after deployment of a prosthesis therefrom, as similarly described above with reference to the embodiment of FIG. 1.

Magnetized element 420 is of a material that acts or may be made to act like a magnet, and may in embodiments hereof be a magnet, and magnetic element 422 is of a material that is attracted by or to magnetized element 420, such as a suitable biocompatible ferrous material. In an embodiment, magnetized element 420 is a magnetized metal band, such as a magnetizable band of a stainless steel alloy, that encircles shelf segment 410b and magnetic element 422 is a stainless steel marker or a magnet that is attached at distal opening 409 of tubular sheath 404. In embodiments hereof, a stainless steel 400 series alloy, which contains steel and chromium, but without the presence of nickel, and an Inox 08 alloy, which is a medical stainless steel composed of carbon, manganese, chromium, molybdenum and vanadium, exhibit magnetic qualities suitable for use herein as magnetized element 420. In another embodiment, a magnetized element may be positioned around distal opening 409 and a magnetic element may be disposed around or within shelf segment 410b without departing from the scope hereof.

Figure 10:
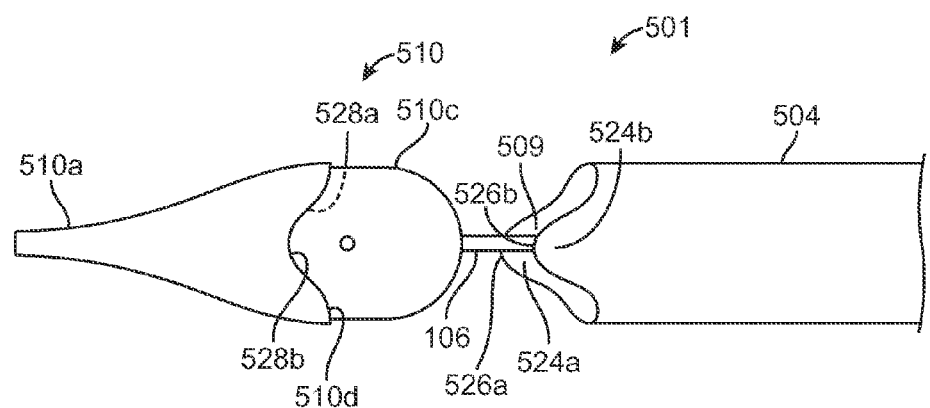
FIG. 10 is a side view of a distal portion of a delivery catheter in a deployment configuration in accordance with an embodiment hereof.
Figure 10A:
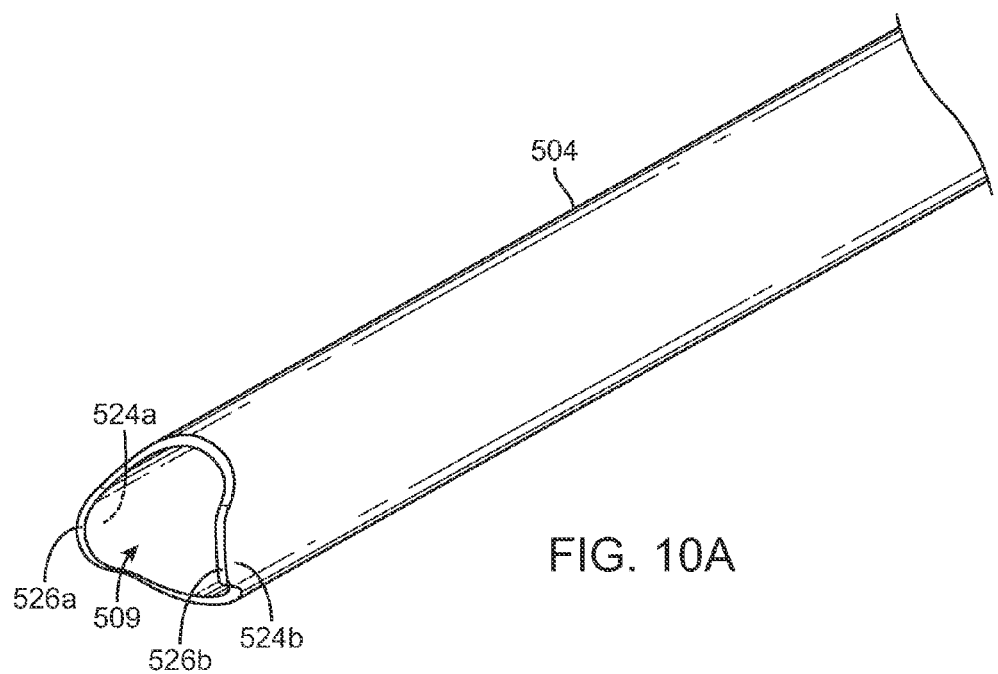
FIG. 10A is a perspective view of a distal portion of a sheath component in accordance with an embodiment hereof removed from the delivery catheter distal portion of FIG. 10.
Figure 11:
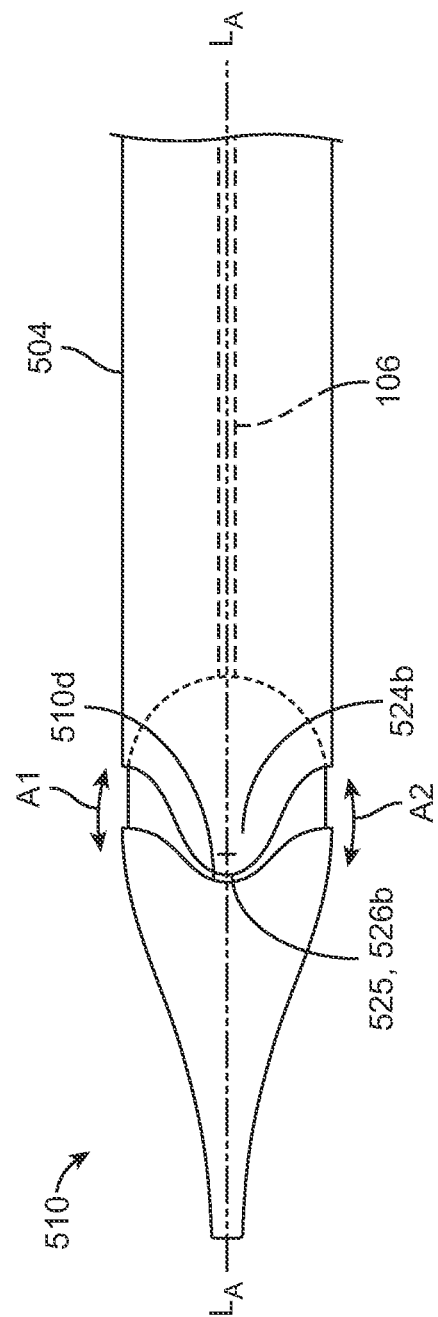
FIG. 11 depicts the delivery catheter distal portion shown in FIG. 11 in a delivery configuration.

FIG. 10 is a side view of a distal portion 501 of delivery catheter 100 in a deployment configuration in accordance with an embodiment hereof, with FIG. 11 depicting the delivery catheter distal portion 501 in a delivery configuration. Further FIG. 10A depicts a perspective view of a distal portion of a modified sheath component 504 removed from the delivery catheter distal portion 501. Distal tip 510 and modified sheath component 504 are described herein as alternate components of delivery catheter 100. Although not shown with a distal capsule section or a funnel segment, it would be understood by one of skill in the art that such features as described with reference to earlier embodiments may be adapted for use in the current embodiment. As well it would be understood to one of skill in the art that the embodiment of FIGS. 10 and 11 may be adapted for use with features described with reference to other embodiments hereof and only features and functions that differ from those described with reference to other embodiments will be detailed herein. As described in the previous embodiments, distal tip 510 defines a guidewire lumen therethrough that is a continuation of guidewire lumen 103 of inner shaft 106 and is attached to inner shaft 106 in any suitable manner as previously described above.

Tubular sheath 504 defines distal opening 509 and distally extending first and second arched portions 524a, 524b. Distal tip 510 engages with distal opening 509 of sheath component 504 when the delivery catheter is in a delivery configuration and disengages from distal opening 509 when the delivery catheter is in a deployment configuration. Distal tip 510 is a molded component having a distal segment 510a and a proximal segment 510c that are demarcated by a proximally facing bearing surface 510d that forms a radially extending circumferential ridge around the distal tip. Distal tip distal segment 510a is distally tapered and distal tip proximal segment 510c has a dome shape that is sized to be slidably receivable within distal opening 509 of sheath component 504.

The circumferential ridge of distal tip 510 defines distally extending first and second valley portions 528a, 528b (with valley portion 528a being hidden from view in FIGS. 10 and 11) that receive at least a crown 526a, 526b of a corresponding first or second arched portion 524a, 524b therein, when distal tip 510 engages with distal opening 509 of sheath component 504 in the delivery configuration. Sheath component 504 includes a distally facing bearing surface 525 that is at least partially defined along a distal surface of crowns 526a, 526b of first and second arched segments 524a, 524b to abut against distal tip bearing surface 510d within the corresponding first and second valley portions 528a, 528b when distal tip 510 engages with distal opening 509 in the delivery configuration. Bearing engagement between first and second valley portions 528a, 528b of distal tip 510 and the corresponding crowns 526a, 526b of first and second arched segments 524a, 524b permits distal tip 510 to slightly pivot or rock back and forth relative to a longitudinal axis $L_4$ of the delivery catheter, as depicted by arrows A1 and A2 in FIG. 11, at an interface with distally facing bearing surface 525 of sheath component 504 to permit bending in a single plane between distal tip 510 and sheath component 504 without separation of the components, or stated another way while maintaining contact between the components. Thus the combination of dome shaped proximal segment 510c of distal tip 510 being received within distal opening 509 of sheath component 504 and the bending permitted at the bearing interface of distal tip 510 and sheath component 504, which is due to the configuration of the corresponding engaging structures thereof, permits distal tip 510 to be retained within distal opening 509 so as to prevent separation and/or fish-mouthing. Accordingly, the embodiment of FIGS. 10 and 11 realizes one or more of the objectives of embodiments hereof, which includes safer tracking of the delivery catheter through the vasculature, safe crossing of the delivery catheter through structural components of the vasculature and heart, such as through native valves, and safe removal of the delivery catheter post deployment.

The delivery devices shown and described herein can be modified for delivery of balloon-expandable stented prosthetic heart valves or any other self-expanding or balloon-expandable prostheses to be delivered endoluminally, within the scope of the present disclosure.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A delivery catheter for endoluminal delivery of a prosthesis comprising:
    a tubular sheath component defining a distal opening and distally extending first and second arched portions, wherein the distal opening is defined by and between the distally extending first and second arched portions;
    an elongate inner shaft at least partially disposed within the sheath component; and
    a distal tip attached to the inner shaft that engages with the distal opening of the sheath component when the delivery catheter is in a delivery configuration and disengages from the distal opening when the delivery catheter is in a deployment configuration, the distal tip defining a distal segment and a proximal segment that are demarcated by a proximally facing bearing surface that forms a radially extending circumferential ridge that continuously extends around the entire circumference of the distal tip,
    wherein the circumferential ridge defines distally extending first and second valley portions that receive at least a crown of a corresponding first or second arched portion of the sheath component therein when the distal tip engages with the distal opening of the sheath component in the delivery configuration.

2. The delivery catheter of claim 1, wherein the sheath component includes a distally facing bearing surface that is at least partially defined along a distal surface of the first and second arched segments to abut against the distal tip bearing surface within the corresponding first and second valley portions when the distal tip engages with the distal opening of the sheath component in the delivery configuration.

3. The delivery catheter of claim 2, wherein bearing engagement between the first and second valley portions of the distal tip and the corresponding crowns of the first and second arched segments permits the distal tip to pivot or rock back and forth on the distally facing bearing surface of the sheath component.

4. The delivery catheter of claim 1, wherein the distal segment of the distal tip is distally tapered and the proximal segment of the distal tip has a dome shape that is sized to be slidably receivable within the distal opening of the sheath component.

5. The delivery catheter of claim 1, wherein the distal segment of the distal tip has a first radiopacity and the proximal segment of the distal tip has a second radiopacity.

* * * * *